US008797724B2

(12) United States Patent
Andrews et al.

(10) Patent No.: US 8,797,724 B2
(45) Date of Patent: Aug. 5, 2014

(54) NOTIFICATION APPLIANCE ENCLOSURE

(75) Inventors: Alexander S. Andrews, Clinton, MA (US); Erick Russell, Windham, NH (US); James T. Roberts, Amherst, NH (US)

(73) Assignee: Tyco Fire & Security GmbH, Neuhausen am Rheinfall (CH)

( * ) Notice: Subject to any disclaimer, the term of this patent is extended or adjusted under 35 U.S.C. 154(b) by 165 days.

(21) Appl. No.: 13/610,801

(22) Filed: Sep. 11, 2012

(65) Prior Publication Data

US 2014/0070678 A1 Mar. 13, 2014

(51) Int. Cl.

| | |
|---|---|
| ***H05K 5/00*** | (2006.01) |
| ***H05K 7/00*** | (2006.01) |
| ***G06F 1/16*** | (2006.01) |
| ***G01N 21/00*** | (2006.01) |
| ***G01N 27/00*** | (2006.01) |
| ***G01N 31/00*** | (2006.01) |
| ***G01N 33/00*** | (2006.01) |
| ***G01N 35/00*** | (2006.01) |
| ***G01N 37/00*** | (2006.01) |
| ***G01D 11/24*** | (2006.01) |
| ***G01L 19/14*** | (2006.01) |
| ***G01P 1/02*** | (2006.01) |
| ***H04M 11/04*** | (2006.01) |
| ***G08B 21/00*** | (2006.01) |
| ***G08B 17/12*** | (2006.01) |
| ***G08B 17/10*** | (2006.01) |

(52) U.S. Cl.

USPC ...... 361/679.01; 73/1.06; 73/431; 455/404.1; 340/540; 340/577; 340/628

(58) Field of Classification Search

USPC ............. 361/679.01, 679.55, 679.56, 679.57, 361/679.58, 679.59; 73/1.06, 431; 455/404.1; 340/628, 540, 577; 312/223.1, 223.2

See application file for complete search history.

(56) References Cited

U.S. PATENT DOCUMENTS

| | | | | |
|---|---|---|---|---|
| 4,384,488 | A * | 5/1983 | Scheidweiler | 73/431 |
| 4,475,390 | A * | 10/1984 | Scheidweiler | 73/431 |
| 6,504,707 | B2 * | 1/2003 | Agata et al. | 361/679.05 |
| 2002/0145847 | A1 * | 10/2002 | Crosby | 361/683 |
| 2004/0090742 | A1 * | 5/2004 | Son et al. | 361/686 |
| 2004/0114319 | A1 * | 6/2004 | Hill et al. | 361/683 |
| 2009/0266183 | A1 * | 10/2009 | Hall et al. | 73/865.9 |
| 2011/0072882 | A1 * | 3/2011 | Hall et al. | 73/23.2 |
| 2012/0171987 | A1 * | 7/2012 | Newman | 455/404.1 |

* cited by examiner

*Primary Examiner* — Anthony Haughton

(74) *Attorney, Agent, or Firm* — Kacvinsky Daisak Bluni PLLC

(57) ABSTRACT

A notification appliance enclosure that facilitates convenient attachment and removal of a housing. The enclosure may include a mounting plate having a catch lip and a retaining wedge projecting from a surface thereof. The catch lip and the retaining wedge may be spaced apart to define a retaining pocket therebetween, and the catch lip may have a latch release aperture formed therethrough. A housing may fit over the mounting plate and may have a latch tongue extending from a surface thereof fits within the retaining pocket. A release latch may extend from a surface of latch tongue and may fit within the latch release aperture. The engagement between the release latch and the latch release aperture prevents the housing from being pulled away from the mounting plate. The retaining wedge resists movement of the latch tongue and thereby resists disengagement of the release latch from the latch release aperture.

18 Claims, 9 Drawing Sheets

NOTIFICATION APPLIANCE ENCLOSURE

FIELD OF THE DISCLOSURE

The disclosure relates generally to the field of notification appliances, and more particularly to a notification appliance enclosure having a housing that can be quickly and easily attached and detached from its base.

BACKGROUND OF THE DISCLOSURE

Emergency notification systems typically include a plurality of notification appliances, such as strobes and horns, for providing occupants of a building with a prominent visual or auditory indication of a hazardous condition, such as the presence of smoke or fire. It is not uncommon for notification systems to include dozens, or even hundreds, of notification appliances distributed throughout a building. Servicing such a large number of appliances can be tedious and time-consuming, especially if uninstalling and reinstalling each appliance involves a lengthy or complicated process.

Typically, a notification appliance is attached to an electrical backbox, which is, in turn, mounted on a wall or ceiling surface (e.g., surface mounted or wire mold mounted) or embedded in a wall. Electrical leads or wires extend from a notification system circuit into the backbox through knockouts in the rear or sides of the backbox. A mounting plate is typically used to attach a notification appliance to the front of the backbox, with audible and/or visual alarm-generating elements of the notification appliance fastened to the mounting plate and having electrical leads extending through the mounting plate and into the backbox. A housing or faceplate is typically placed over the notification appliance and is fastened to the back plate for providing the notification appliance with a secure enclosure.

Many conventional notification appliance enclosures have housings that are secured with one or more screws or other mechanical fasteners that must be fastened and unfastened with a tool during mounting and removal of the housing, respectively. Such fastening and unfastening can take an undesirably long amount of time, especially when aggregated over a large number of appliances. Nonetheless, screws and other such fasteners are commonly employed to provide appliance enclosures with sufficient robustness to satisfy industry standards. For example, Underwriters Laboratories (UL) requires that notification appliance enclosures be able to withstand certain impact forces without opening or being significantly damaged.

In view of the foregoing, it would be desirable to provide a robust notification appliance enclosure that can be opened and closed in a relatively short period of time (e.g. less than five seconds), with relatively little effort and without the use of specialized tools or separate fasteners. The design should provide this easy access while also being robust enough to meet existing UL impact standards.

SUMMARY

A notification appliance enclosure is disclosed. The notification appliance enclosure may include a mounting plate having a catch lip and a retaining wedge projecting from a surface thereof. The catch lip and the retaining wedge may be spaced apart to define a retaining pocket therebetween. The catch lip may have a latch release aperture formed therethrough. The enclosure may also include a housing adapted to fit at least partially over the mounting plate. The housing may have a latch tongue extending from a surface thereof. The latch tongue may be configured to be received within the retaining pocket when the housing and the mounting plate are connected to one another. The latch tongue may have a release latch extending from a surface thereof, and the release latch may be configured to be received within the latch release aperture of the mounting plate when the housing and the mounting plate are connected to one another. The retaining wedge may be configured to receive the latch tongue to resist lateral movement of the latch tongue and to resist disengagement of the release latch from the latch release aperture when the housing and the mounting plate are connected to one another.

A notification appliance enclosure assembly is disclosed. The assembly may include a mounting plate having a catch lip and a first and second retaining wedges projecting from a surface thereof. The catch lip and the first and second retaining wedges may be spaced apart to define a retaining pocket therebetween. The catch lip may have a latch release aperture formed therethrough. The assembly may also include a housing adapted to fit at least partially over the mounting plate. The housing may have a latch tongue configured to be received within the retaining pocket. The latch tongue may have a release latch extending from a surface thereof. The release latch may be configured to be received within the latch release aperture of the mounting plate. Thus arranged, when the mounting plate and housing are coupled together, the first and second retaining wedges may resist movement of the latch tongue and resists disengagement of the release latch from the latch release aperture.

BRIEF DESCRIPTION OF THE DRAWINGS

By way of example, specific embodiments of the disclosed device will now be described, with reference to the accompanying drawings, in which.

DETAILED DESCRIPTION

Figure 1:
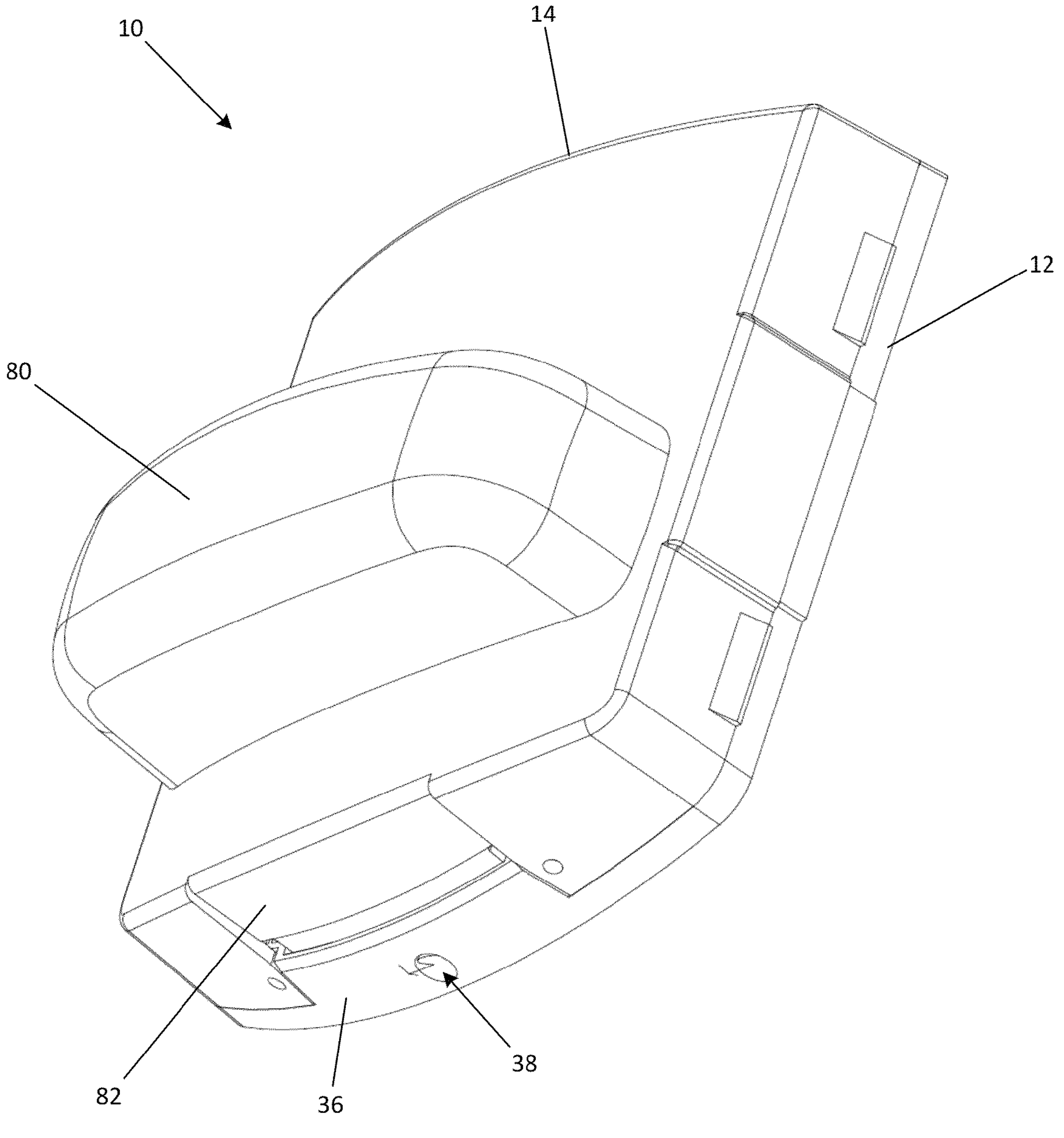
FIG. 1 is a perspective view illustrating an embodiment of a notification appliance enclosure in accordance with the present disclosure.
Figure 2:
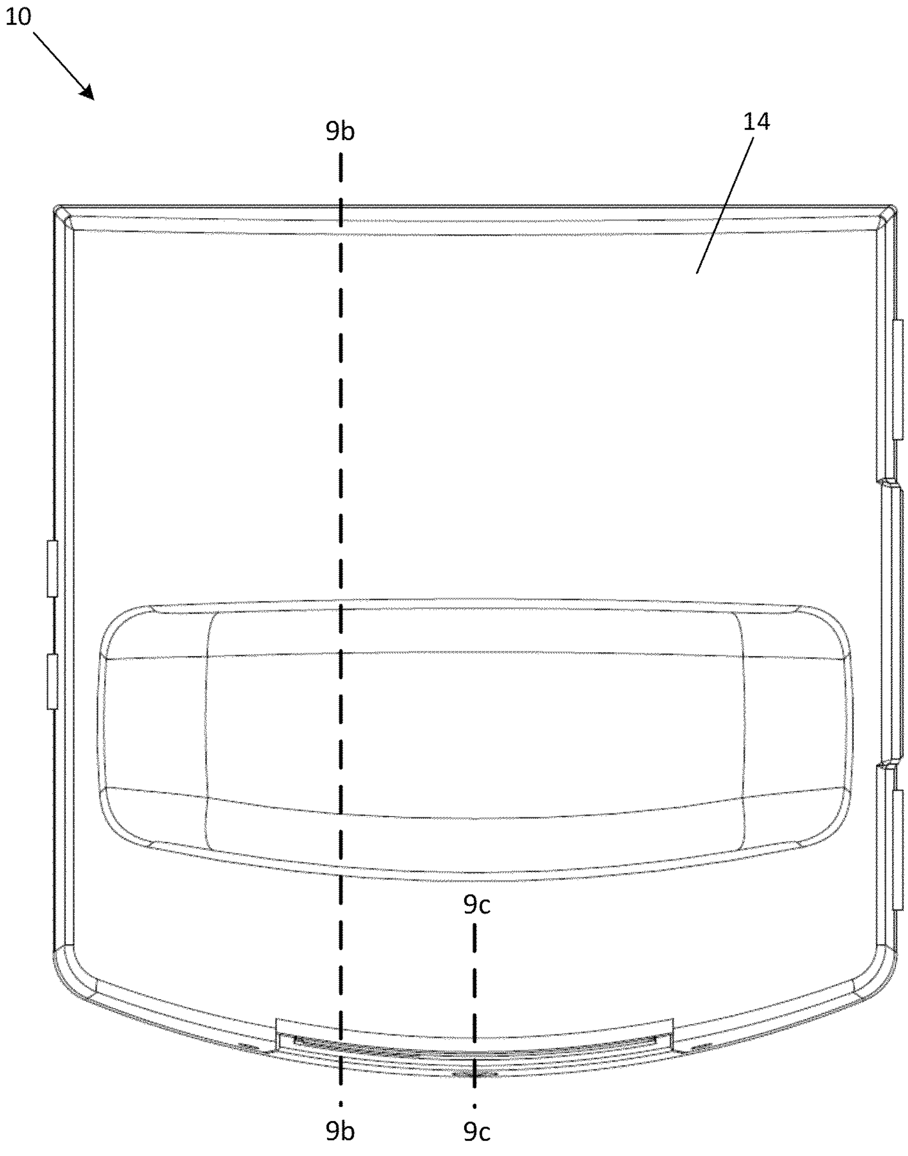
FIG. 2 is a front view illustrating an embodiment of the notification appliance enclosure shown in FIG. 1.

Referring to FIGS. 1 and 2, a notification appliance enclosure 10 (hereinafter referred to as "the enclosure 10") in accordance with the present disclosure is shown. The enclosure 10 is provided for facilitating convenient and expeditious installation and uninstallation of a notification application housed therein. The enclosure 10 can be used in conjunction with virtually any type of notification appliance, including, but not limited to, various types of strobes, digital displays, horns, buzzers, chimes, bells, speakers, and various combinations thereof. Any particular notification appliances that are described herein are therefore provided by way of example only and are not meant to be limiting in any way.

For the sake of convenience and clarity, terms such as "front," "rear," "top," "bottom," "up," "down," "inwardly," "outwardly," "lateral," and "longitudinal" will be used herein to describe the relative placement and orientation of components of the enclosure 10, each with respect to the geometry and orientation of the enclosure 10 as it appears in FIGS. 1 and 2. Said terminology will include the words specifically mentioned, derivatives thereof, and words of similar import.

Referring to FIGS. 1 and 2, the enclosure 10 may include a mounting plate 12 and a housing 14. It is contemplated that the mounting plate 12 and the housing 14 may be formed partially or entirely of various plastics, metals, or composites that are suitably durable and resilient for being formed and manipulated in the manner described herein. It is further contemplated that the mounting plate 12 and the housing 14 may be formed of the same material or different materials.

Referring to FIGS. 1 and 3-5, the mounting plate 12 may be a substantially rectangular and substantially planar member. The mounting plate 12 may have a plurality of apertures 16 formed therethrough for allowing the mounting plate 12 to be attached to various standard backboxes (not shown) with conventional fasteners. Such backboxes may include, but are not limited to, a single-gang box, a double-gang box (either surface mounted or wire mold mounted), and a 4-inch box. It is contemplated that the size and shape of the mounting plate 12 and the configuration of the apertures 16 can be adapted to accommodate backboxes of various shapes, including, but not limited to, octagon-shaped backboxes (e.g., 3.5 inch or 4 inch octal backbox), international (100 mm) boxes, and the like. An installer may thus deploy the mounting plate 12 in the field irrespective of particular backboxes that are present at a particular application site. This compatibility with various backboxes increases ease of installation and simplifies the ordering of mounting plates for a particular installation project.

The mounting plate 12 may include a wiring aperture 18 formed therethrough for allowing notification system wiring to extend from a backbox into the enclosure 10 for connection to a notification appliance. Such wiring may provide a notification appliance with electrical power and may allow the notification application to communicate with other components of a notification system. It will be appreciated by those of ordinary skill in the art that the mounting plate 12 may further include various other apertures, recesses, channels, and the like for accommodating the structural features and wiring of a particular notification appliance that is mounted within the enclosure 10.

The mounting plate 12 may include a plurality of adjoining sidewalls 20, 22, 24, 26, and 28 that may extend forward from a front surface 30 of the mounting plate, inward of the mounting plate's outermost edges, to define a recessed shoulder 32 that extends substantially around a periphery of the mounting plate 12 except for a center portion of the lower edge 34 of the mounting plate 12 (described in greater detail below). The lower edge 34 and lower sidewalls 24 and 26 of the mounting plate 12 may be formed with a convex curvature as shown, but this is not critical, and thus, the lower edge 34 and lower sidewalls 20-28 may alternatively be straight, concave, or angled, for example.

The non-recessed center portion of the lower edge 34 (located intermediate the sidewalls 24 and 26) may define a catch lip 36 (FIG. 4) that projects outward from the front surface 30 of the mounting plate 12 below the sidewalls 24 and 26. A latch release aperture 38 may be formed through the lateral center of the catch lip 36. The latch release aperture 38 is shown as being circular in shape, but this is not critical, and thus, the latch release aperture 38 may be of any size or shape that may allow an implement, such as the tip of a conventional Phillips or flat head screwdriver, to be inserted therethrough as further described below.

Figure 3:
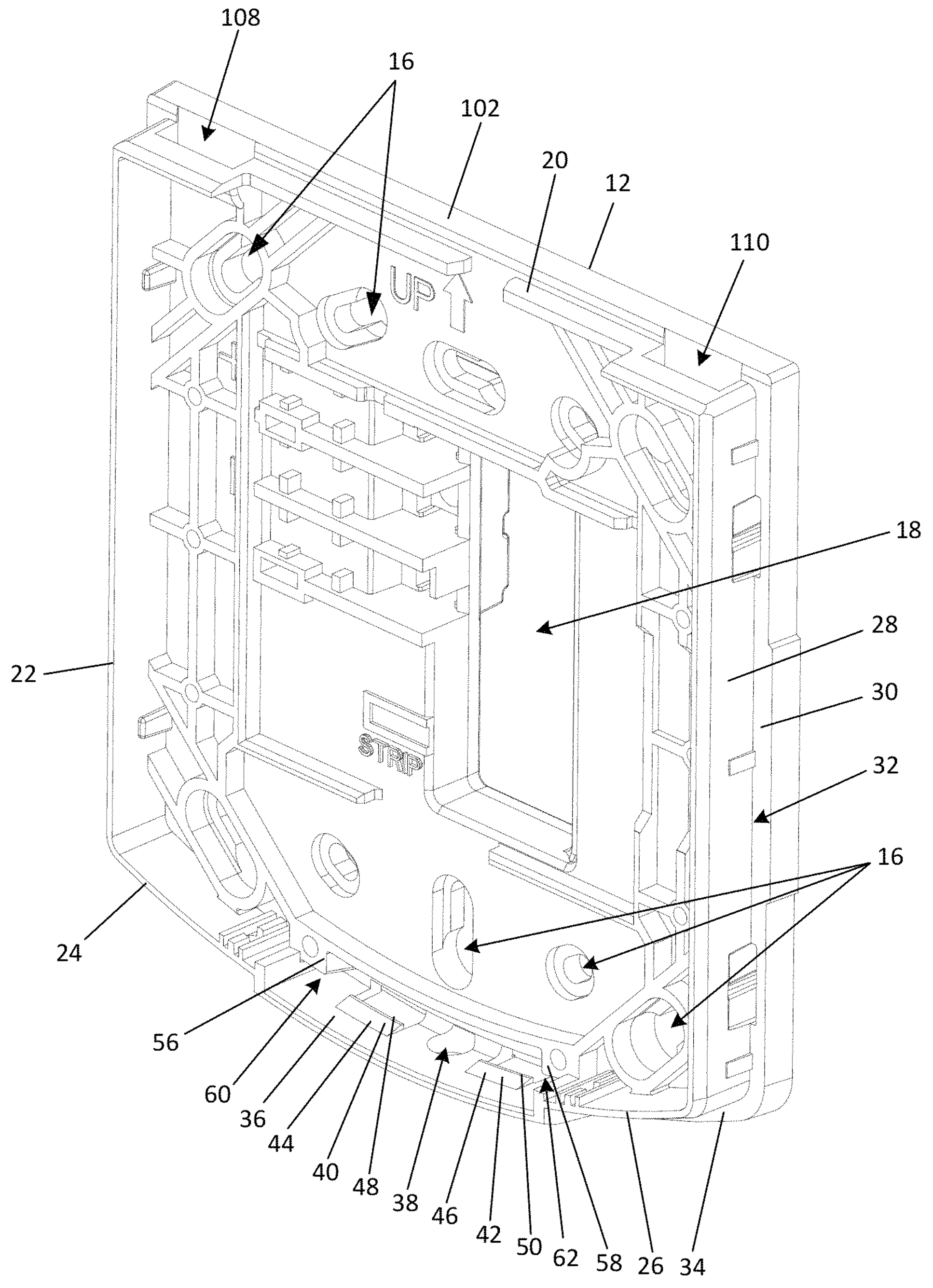
FIG. 3 is a front perspective view illustrating an embodiment of a mounting plate of the notification appliance enclosure shown in FIG. 1.
Figure 5:
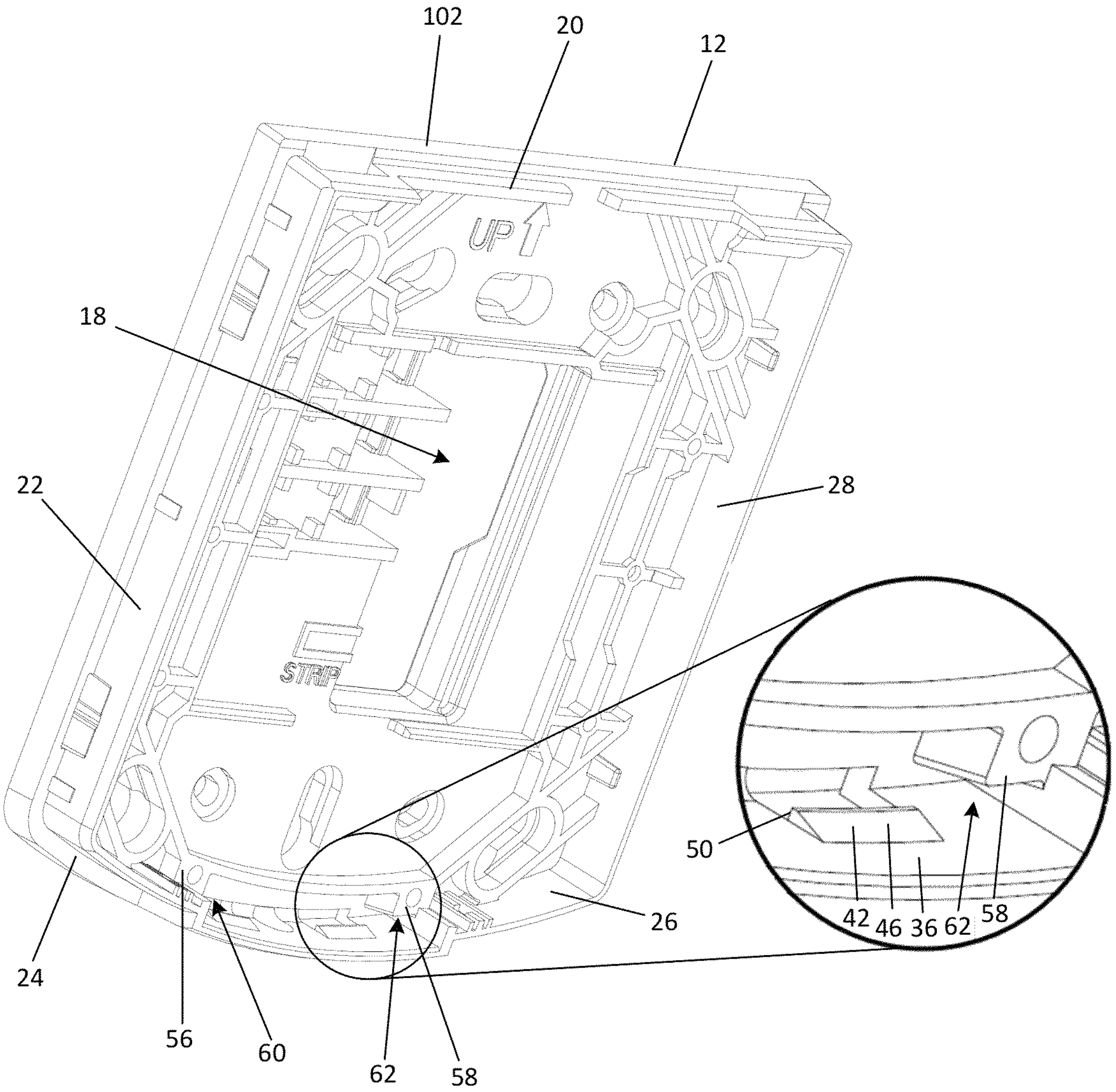
FIG. 5 is a reverse perspective view illustrating an embodiment of the mounting plate shown in FIG. 1.

As best shown in FIGS. 3 and 5, retaining catches 40 and 42 may extend upwardly from a top surface of the catch lip 36 on either lateral side of the latch release aperture 38. The retaining catches 40 and 42 may have an inclined top surface 44, 46 (i.e., inclined from front to rear) and a vertically-oriented rear wall 48, 50. It is contemplated, however, that the shape and configuration of the retaining catches 40 and 42 may be varied without departing from the present disclosure. In addition, while two retaining catches 40 and 42 are shown, embodiments of the mounting plate 12 are contemplated in which only one, or where more than two, retaining catches are provided. It is further contemplated that the retaining catches 40 and 42 may be entirely omitted.

Figure 4:
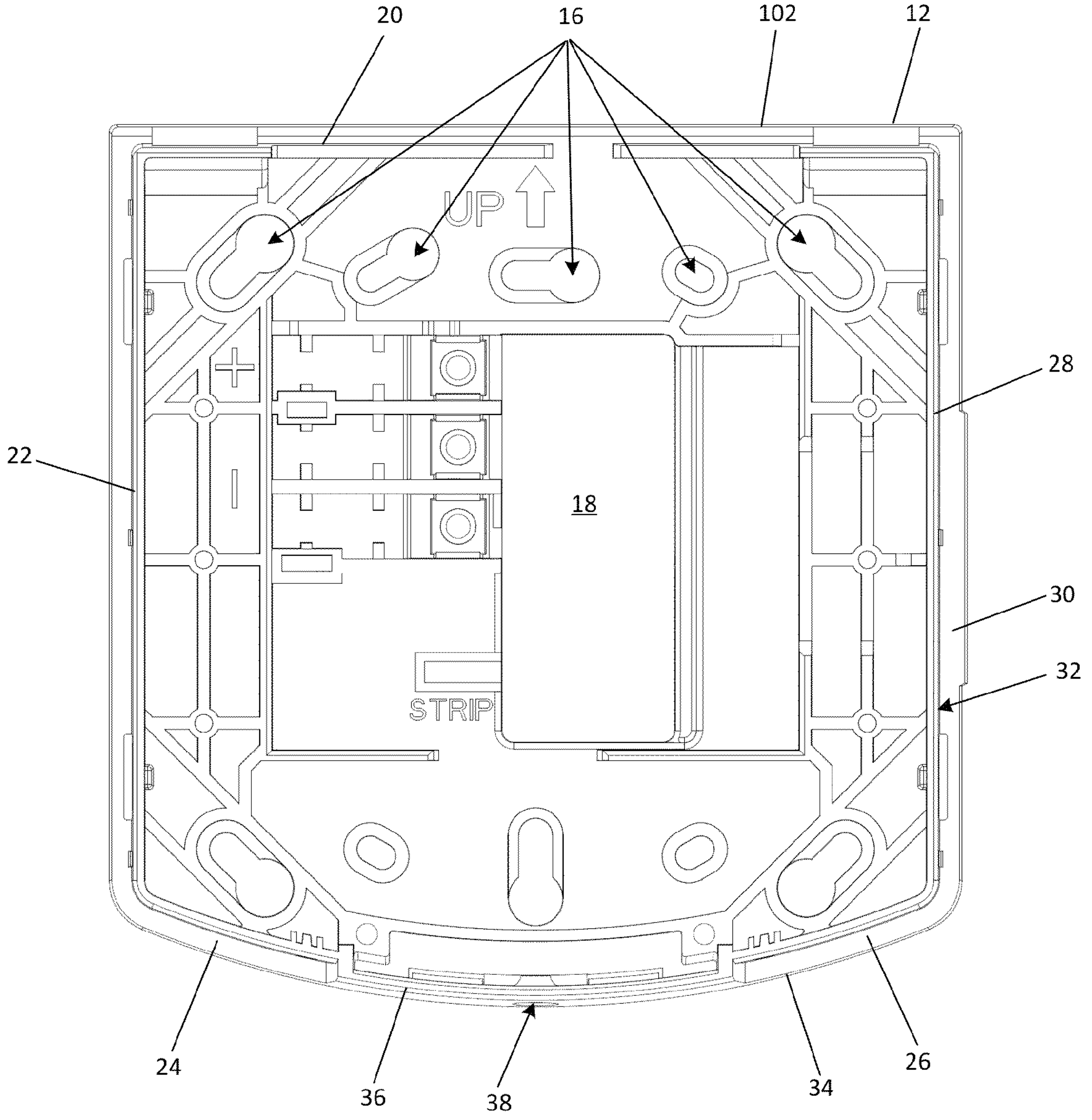
FIG. 4 is a front view illustrating an embodiment of the mounting plate shown in FIG. 3.

Referring to FIGS. 3-5, a pair of retaining wedges 56 and 58 may project forward from the front surface 30 of the mounting plate 12. The retaining wedges 56 and 58 may be positioned above and laterally outward of the retaining catches 40 and 42. A lower surface of each retaining wedge 56 and 58 may be spaced apart from the top surface of the catch lip 36 to define a receiving pocket 60 and 62 therebetween. The lower surfaces of the retaining wedges 56 and 58 may be angled downwardly from front to back toward the catch lip 36 so that the receiving pockets 60 and 62 decrease in size from front to back. Alternatively, it is contemplated that the lower surfaces of the retaining wedges 56 and 58 may be parallel with the top surface of the catch lip 36 so that the receiving pockets 60 and 62 are a consistent size from front to back.

Figure 6:
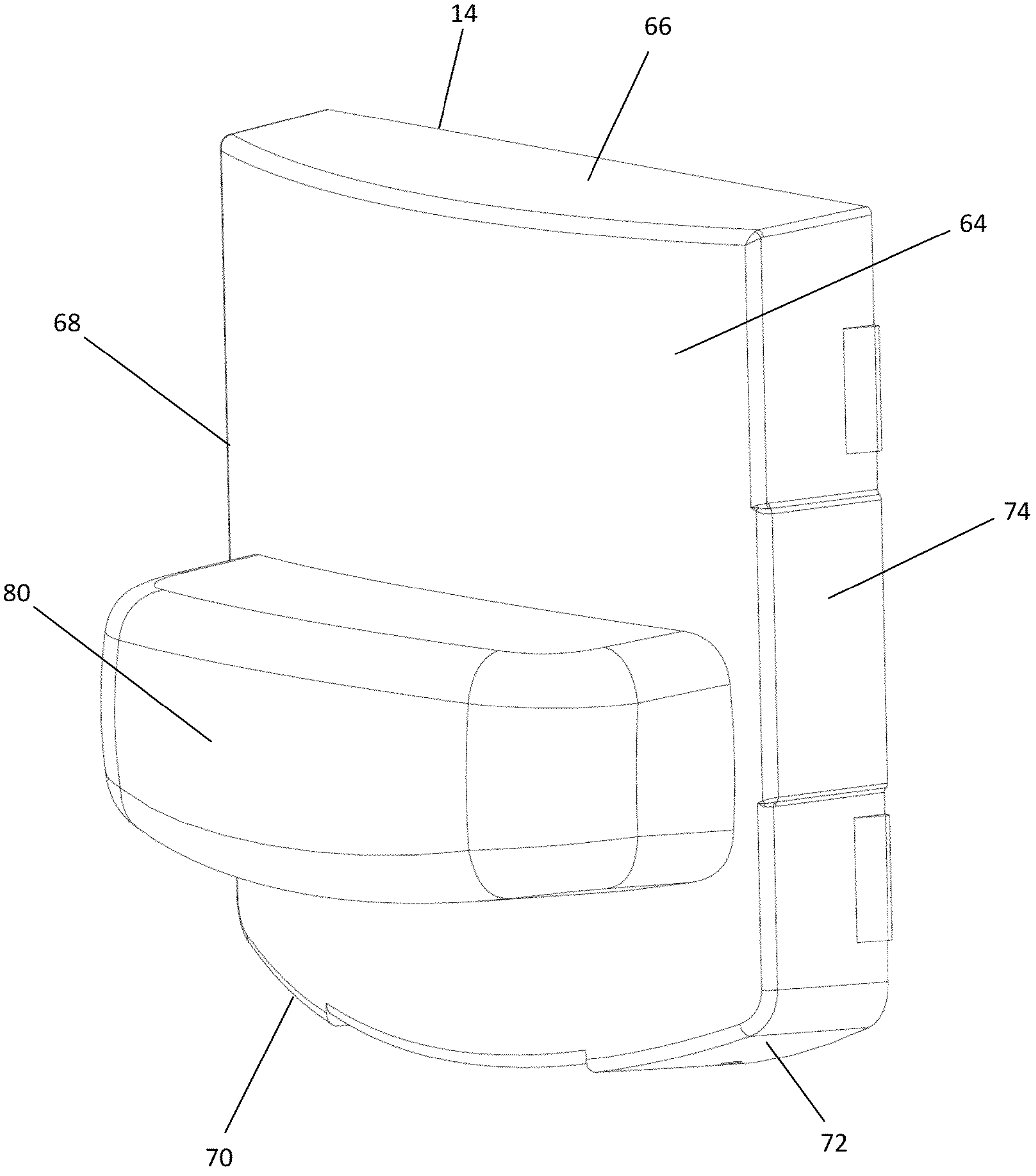
FIG. 6 is a front perspective view illustrating an embodiment of the housing portion of the notification appliance enclosure shown in FIG. 1.
Figure 7:
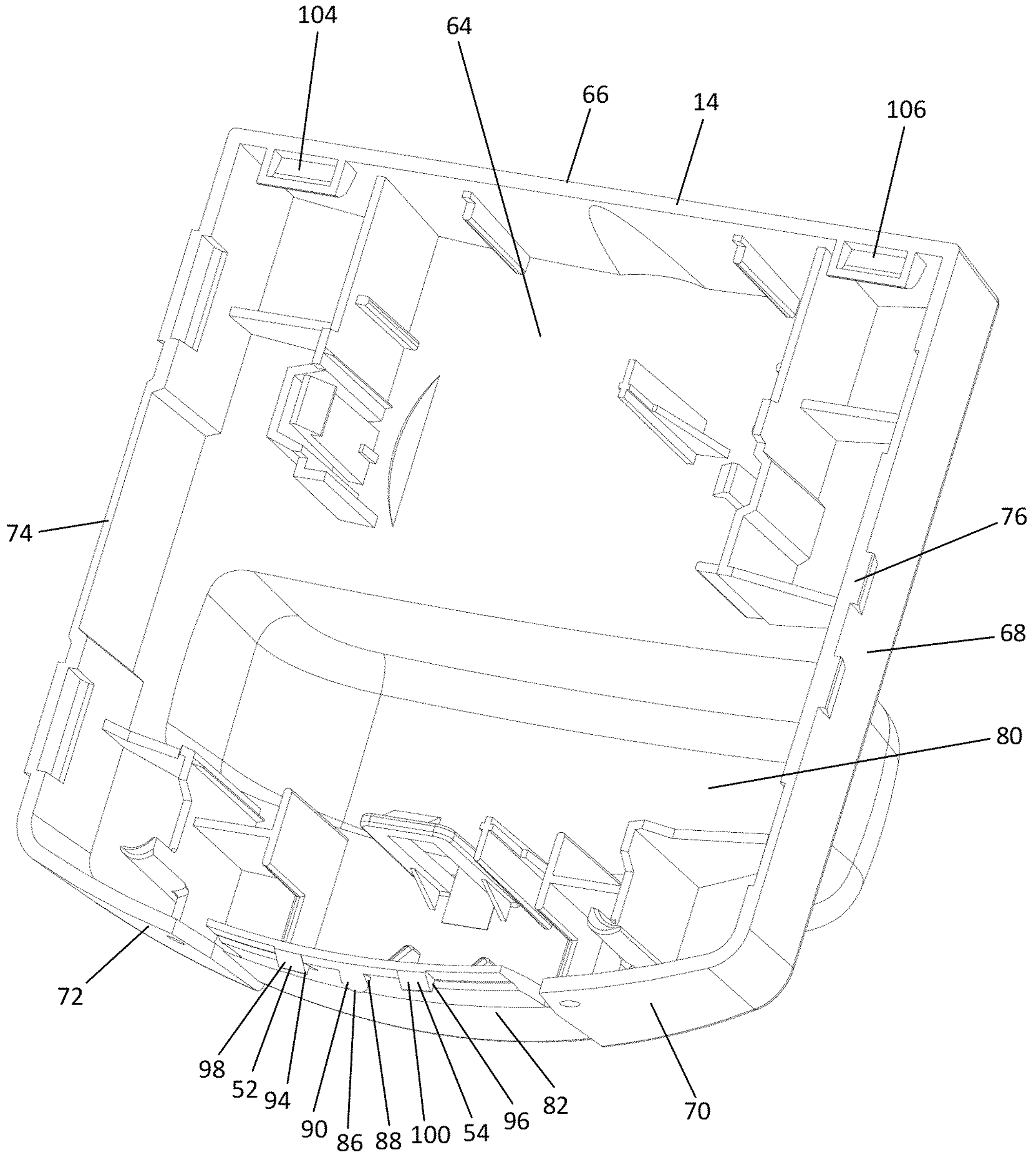
FIG. 7 is a rear perspective view illustrating the housing of the notification appliance shown in FIG. 6.
Figure 8:
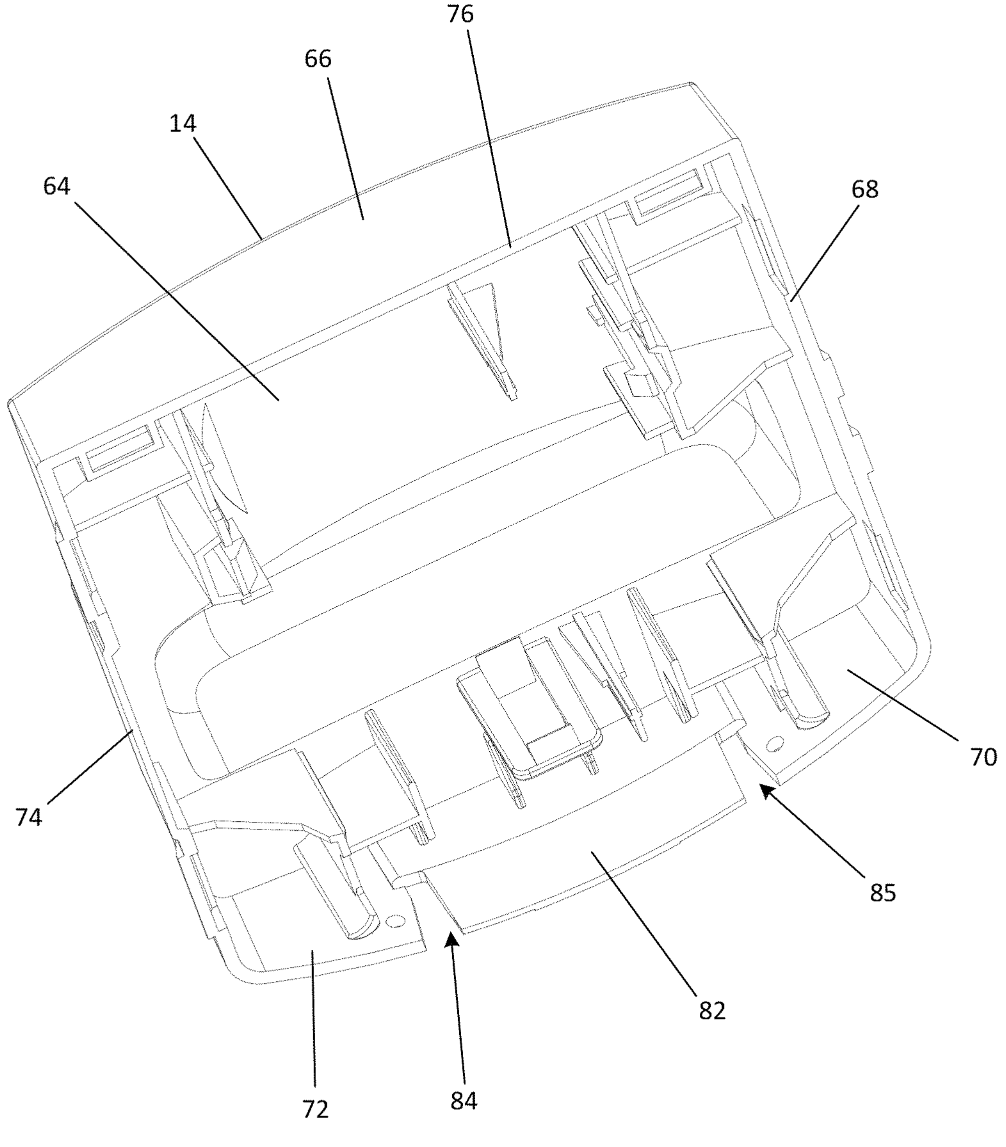
FIG. 8 is a reverse perspective view illustrating the housing of the notification appliance enclosure shown in FIG. 6.

Referring to FIGS. 6-8, the housing 14 of the enclosure 10 may be defined by a substantially rectangular front wall 64 and adjoining sidewalls 66, 68, 70, 72, and 74 that extend from the edges thereof. The rear edges of the sidewalls 66-72 define a rearmost, planar lip 76 that extends substantially around a periphery of the rear of the housing 14 except for a center portion intermediate the lower sidewalls 70 and 72, as will be described in greater detail below. The lower sidewalls 70 and 72 of the housing 14 may be formed with a convex curvature to match the convex curvature of the lower edge 34 and lower sidewalls 24 and 26 of the mounting plate 12. Of course, if the mounting plate 12 is formed with a different shape, such as straight, concave, or angled, the housing 14 may be formed with a complementary shape for fitting over the mounting plate 12.

The front wall 64 of the housing 14 may include a convex protrusion 80 (FIG. 7) formed of a substantially transparent material, such as transparent thermoplastic, for receiving and providing clear visibility of a strobe or other visual notification appliance that is mounted within the enclosure 10. It will be appreciated by those of ordinary skill in the art that the front wall 64 and/or sidewalls 66-72 of the housing 14 may additionally or alternatively include various other protrusions, apertures, perforations, and the like for accommodating the structural and functional features of a particular notification appliance that is mounted within the enclosure 10. For example, the front wall 64 and/or sidewalls 66-72 of the housing 14 may be perforated for allowing an auditory notification appliance, such as a horn, to clearly project sound through the enclosure 10.

Referring to FIGS. 7 and 8, a generally rectangular latch tongue 82 may extend rearward from the lower edge of front wall 64 intermediate the sidewalls 70 and 72. The latch tongue 82 may extend beyond the sidewalls 70 and 72 and may have outer lateral edges that are spaced laterally apart from the inner lateral edges of the sidewalls 70 and 72 to form gaps 84 and 85 therebetween. The curvature of the lower surface of the latch tongue 82 may be substantially similar to the curvature of the upper surface of the catch lip 36 (described above).

Referring to FIG. 7, a release latch 86 may extend downwardly from a lateral center of the lower surface of the latch tongue 82 and may have a size and shape that facilitates mating insertion into the latch release aperture 38 of the catch lip 36 (as further described below). For example, the release latch 86 may have a vertically-oriented, rounded front wall 88 with a curvature that is substantially similar to the curvature of the latch release aperture 38 in the catch lip 36. The release latch 86 may further have an angled lower surface 90 that extends upwardly from a lowermost front edge to meet the rear edge of the latch tongue 82. This angled geometry may facilitate snap insertion of the release latch 86 into the aperture 38 of the catch lip 36. It is contemplated, however, that the shape and configuration of the release latch 86 may be varied without departing from the present disclosure. For example, the front wall 88 of the release latch 86 may be straight instead of rounded and the lower surface 90 of the release latch 86 may be rounded instead of angled.

Retaining latches 52 and 54 may extend downwardly from the lower surface of the latch tongue 82 on either lateral side of, and equidistant from, the release latch 86. The retaining latches 52 and 54 may be separated from one another by a lateral distance that facilitates at least partial alignment with the retaining catches 40 and 42 of the mounting plate 12 when the housing 14 and mounting plate 12 are operatively connected (as described below). For example, the retaining latches 52 and 54 may be separated from one another by a lateral, on-center distance that is approximately equal to the lateral, on-center distance that separates the retaining catches 40 and 42.

The retaining latches 52 and 54 may have straight, vertically-oriented front walls 94 and 96 that form a shoulder with the lower surface of the latch tongue 82 and that may engage the rear walls 48 and 50 of the retaining catches 40 and 42 in a flatly abutting manner when the housing 14 and mounting plate 12 are operatively connected (as described below). The retaining latches 52 and 54 may further have angled lower surfaces 98 and 100 that extend upwardly from a lowermost front terminus to meet the rear edge of the latch tongue 82. It is contemplated that the shape and configuration of the retaining catches 52 and 54 may be varied without departing from the present disclosure. For example, the lower surfaces 98 and 100 of the retaining latches could be rounded instead of angled.

In order to connect the housing 14 to the mounting plate 12, the top sidewall 66 of the housing 14 will generally first be pivotably engaged with the top edge 102 or sidewall 20 of the mounting plate 12. Such connection may be facilitated by various types of permanent or removable attachment. For example, referring to FIGS. 3 and 7, the top sidewall 66 of the housing 14 may have a pair of tabs 104 and 106 extending inwardly therefrom that may be inserted into a pair of correspondingly-positioned slots 108 and 110 in the top sidewall 20 of the mounting plate 12. The engagement between the tabs 104 and 106 and the slots 108 and 110 may be sufficiently loose (i.e., the tabs 104 and 106 may be sufficiently smaller than the slots 108 and 110) to allow the housing 14 to be pivoted about the top sidewall 20 of the mounting plate 12 while maintaining engagement between the tabs 104 and 106 and the slots 108 and 110. Alternatively, the top sidewall 66 of the housing 14 may be permanently connected to the top edge 102 of the mounting plate 12, such as with a conventional hinge, or with a living hinge.

Figure 9A:
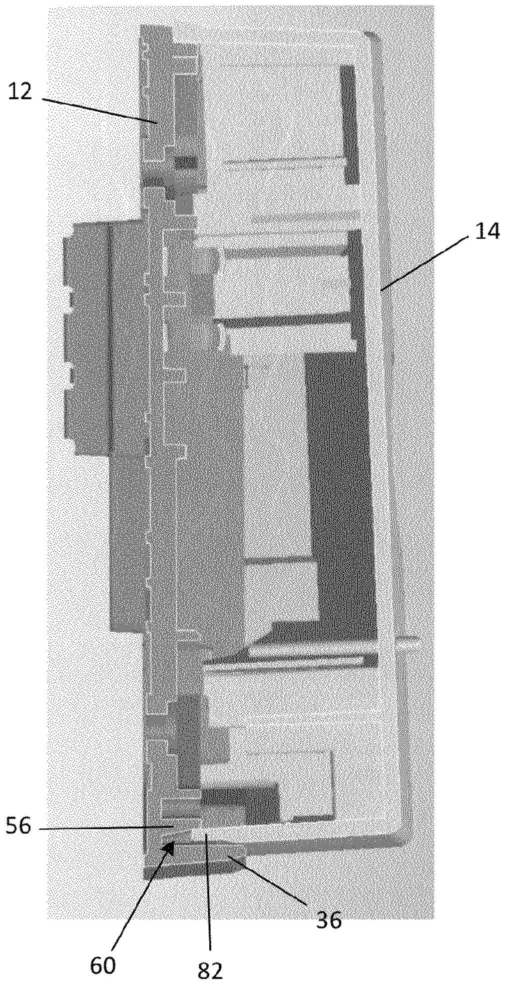
FIG. 9*a* is cross-section view of notification appliance enclosure shown in FIG. 1, taken along line 9*b*-9*b* of FIG. 2, illustrating partial engagement between the latch tongue of the housing and the retaining pocket of the mounting plate.

After the top sidewall 66 of the housing 14 is connected in the aforementioned manner to the top edge 102 or sidewall 20 of the mounting plate 12, the latch tongue 82 of the housing 14 may be pivoted downwardly into preliminary engagement with catch lip 36 of the mounting plate 12. This is shown in FIG. 9*a*. As can be seen, the leading edge of the latch tongue 82 is partially inserted into the retaining pocket 60 (and 62, though not visible in this view), vertically intermediate the retaining wedge 56 (and 58, again, not visible in this view) and the top surface of the catch lip 36. With the latch tongue 82 inserted into the retaining pockets 60 and 62, the upwardly-angled lower surfaces 90, 98, and 100 of the release latch 86 and retaining latches 52 and 54 may then be brought into engagement with the front edge of the catch lip 36.

By applying rearwardly-directed manual force to a lower portion of the housing 14, the catch lip 36 may, through engagement with the angled lower surfaces 90, 98, and 100 of the release latch 86 and retaining latches 52 and 54, forcibly flex or deflect the latch tongue 82 upwardly so that the release latch 86 and retaining latches 52 and 54 are able to pass over the front edge of the catch lip 36 and slide along the top surface of the catch lip 36. After sliding a short distance in this manner, the upwardly-angled lower surfaces 98 and 100 of the retaining latches 52 and 54 are brought into engagement with the upwardly-angled top surfaces 44 and 46 of the retaining catches 40 and 42.

Figure 9B:
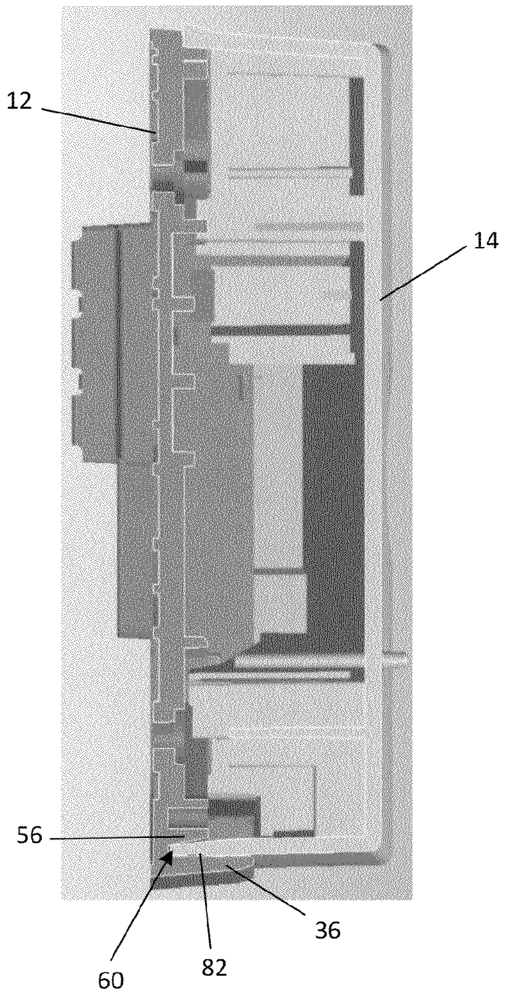
FIG. 9*b* is a cross-section view of notification appliance enclosure similar to that of FIG. 9*a* illustrating complete engagement between the latch tongue of the housing and the retaining pocket of the mounting plate.
Figure 9C:
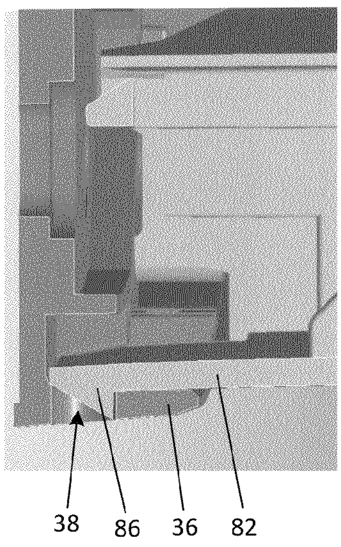
FIG. 9*c* is partial cross-section view of notification appliance enclosure shown in FIG. 1, taken along line 9*c*-9*c* of FIG. 2, illustrating engagement between the release latch of the housing and the latch release aperture of the mounting plate of the notification appliance enclosure shown in FIG. 1.

By applying an additional amount of rearwardly-directed manual force to a lower portion of the housing 14, the retaining catches 40 and 42 may, through engagement with the angled lower surfaces 98 and 100 of the retaining latches 52 and 54, forcibly flex or deflect the latch tongue 82 upwardly. The retaining latches 52 and 54 are thereby able to slide over the retaining catches 40 and 42 until the front walls 94 and 96 of the retaining latches 52 and 54 move over rear walls 48 and 50 of the retaining catches 40 and 42 and the lower surface 90 of the release latch 86 moves over the front edge of the latch release aperture 38, at which point the latch tongue 82 is allowed to move downward, back to its non-deflected position (see FIG. 9*b*). The retaining latches 52 and 54 may drop behind the retaining catches 40 and 42 and the release latch 86 may drop into the latch release aperture 38 as shown in FIG. 9*c*, thus preventing the housing 14 from being pulled in the reverse direction, out of engagement with the mounting plate 12.

With the release latch 86 and retaining latches 52 and 54 secured in the manner described above, the housing 14 is firmly attached to the mounting plate 12 with the rear lip 76 of the housing 14 seated flush against the front surface 30 of the mounting plate 12. The rear edge of the latch tongue 82 is also fully inserted into the retaining pockets 60 and 62 below the retaining wedges 56 and 58 as shown in FIG. 9*b* (retaining wedge 58 and retaining pocket 62 are not within view in FIG. 9). Particularly, the retaining wedges 56 and 58 restrict upward deflection of the outer lateral edges of the latch tongue 82, thereby resisting disengagement of the release latch 86 and the retaining latches 52 and 54 from the latch release aperture 38 and the retaining catches 40 and 42, respectively. Thus arranged, the enclosure 10 may sustain substantial impacts or jarring, such as may be administered during impact force testing, without the housing 14 becoming disengaged from the mounting plate 12. In this way, the housing 14 may be securely attached to the mounting plate 12 in a convenient, expeditious manner that does not require the time-consuming application of mechanical fasteners.

To remove the housing 14 from the mounting plate 12, for example to repair or replace a notification appliance within the enclosure 10, a service person may insert a portion of a tool or implement, such as the tip of screwdriver, into the latch release aperture 38 and bring the tool into engagement with the lower surface 90 of the release latch 86. By applying inwardly-directed force to the release latch 86 with the tool, the release latch 86 may be lifted out of the latch release aperture 38, thereby deflecting the latch tongue 82 upwardly a sufficient amount to lift the retaining latches 52 and 54 above the retaining catches 40 and 42. The bottom of the housing 14 may then be pivoted away from the bottom of the mounting plate 12 without resistance, thereby opening the enclosure 10 providing access to a notification appliance mounted therein. Thus, housing 14 may be separated from the mounting plate 12 in a convenient, expeditious manner without engaging in the time-consuming removal of any mechanical fasteners.

As used herein, an element or step recited in the singular and proceeded with the word “a” or “an” should be understood as not excluding plural elements or steps, unless such exclusion is explicitly recited. Furthermore, references to “one embodiment” of the present invention are not intended to be interpreted as excluding the existence of additional embodiments that also incorporate the recited features.

While certain embodiments of the disclosure have been described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A notification appliance enclosure comprising:

a mounting plate having a catch lip and a retaining wedge projecting from a surface thereof, the catch lip and the retaining wedge spaced apart to define a retaining pocket therebetween, the catch lip having a latch release aperture formed therethrough; and a housing adapted to fit at least partially over the mounting plate, the housing having a latch tongue extending from a surface thereof, the latch tongue configured to be received within the retaining pocket when the housing and the mounting plate are connected to one another, the latch tongue having a release latch extending from a surface thereof wherein the release latch is configured to be received within the latch release aperture of the mounting plate when the housing and the mounting plate are connected to one another;

wherein the retaining wedge is adapted to receive the latch tongue to resist lateral movement of the latch tongue and to resist disengagement of the release latch from the latch release aperture when the housing and the mounting plate are connected to one another.

2. The notification appliance in accordance with claim 1, further comprising a retaining catch extending from a surface of the catch lip and a corresponding retaining latch extending from a surface of the latch tongue, wherein the retaining catch and the retaining latch are configured to engage one another and resist relative movement of the housing and the mounting plate when the housing and the mounting plate are connected to one another.

3. The notification appliance in accordance with claim 1, wherein latch tongue abuts the catch lip when the housing and the mounting plate are connected to one another.

4. The notification appliance in accordance with claim 1, wherein the housing is adapted to be pivotably attached to the mounting plate at an end opposite the catch lip and latch tongue.

5. The notification appliance in accordance with claim 1, wherein the release latch includes an angled lower surface for facilitating snap insertion of the release latch release aperture of the catch lip.

6. The notification appliance in accordance with claim 1, wherein the retaining wedge comprises first and second retaining wedges disposed on opposite lateral sides of the catch lip to create first and second retaining pockets therebetween.

7. The notification appliance in accordance with claim 1, wherein the release latch is actuable via the latch release aperture from an outer surface of the housing.

8. The notification appliance in accordance with claim 1, wherein the release latch is resiliently deformable to enable repeated engagement and disengagement with the mounting plate.

9. The notification appliance in accordance with claim 1, wherein the latch tongue is resiliently deformable to enable repeated engagement and disengagement with the retaining wedge.

10. A notification appliance enclosure assembly comprising:

a mounting plate having a catch lip and a first and second retaining wedges projecting from a surface thereof, the catch lip and the first and second retaining wedges are spaced apart to define a retaining pocket therebetween, the catch lip having a latch release aperture formed therethrough; and a housing adapted that fits at least partially over the mounting plate, the housing having a latch tongue configured to be received within the retaining pocket, the latch tongue having a release latch extending from a surface thereof, wherein the release latch is configured to be received within the latch release aperture of the mounting plate;

wherein when the mounting plate and housing are coupled together, the first and second retaining wedges resists movement of the latch tongue and resists disengagement of the release latch from the latch release aperture.

11. The notification appliance in accordance with claim 10, further comprising a retaining catch extending from a surface of the catch lip and a corresponding retaining latch extending from a surface of the latch tongue, wherein the retaining catch and the retaining latch engage one another to resist relative movement of the housing and the mounting plate.

12. The notification appliance in accordance with claim 10, wherein latch tongue abuts the catch lip.

13. The notification appliance in accordance with claim 10, wherein the housing is pivotably attached to the mounting plate at an end opposite the catch lip and latch tongue.

14. The notification appliance in accordance with claim 10, wherein the release latch includes an angled lower surface for facilitating snap insertion of the release latch release aperture of the catch lip.

15. The notification appliance in accordance with claim 10, wherein the first and second retaining wedges are disposed on opposite lateral sides of the catch lip to create first and second retaining pockets therebetween.

16. The notification appliance in accordance with claim 10, wherein the release latch is disengeable with the housing using a tool inserted through the latch release aperture from an outer surface of the housing.

17. The notification appliance in accordance with claim 10, wherein the release latch is resiliently deformable to enable the release latch to be resiliently engageable with the mounting plate.

18. The notification appliance in accordance with claim 11, wherein the latch tongue is deformable to enable firm engagement with the first and second retaining wedges.

* * * * *